United States Patent
Sawai

(10) Patent No.: US 7,782,456 B2
(45) Date of Patent: Aug. 24, 2010

(54) DIRECT ICP EMISSION SPECTRAL ANALYSIS METHOD OF SOLID SAMPLE

(75) Inventor: Hiroshi Sawai, Ichikawa (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 192 days.

(21) Appl. No.: 12/029,531

(22) Filed: Feb. 12, 2008

(65) Prior Publication Data

US 2008/0198359 A1   Aug. 21, 2008

(30) Foreign Application Priority Data

Feb. 16, 2007  (JP) ............................. P2007-036182

(51) Int. Cl.
   *G01J 3/30*   (2006.01)
(52) U.S. Cl. ...................................................... 356/316
(58) Field of Classification Search .................. 356/36, 356/316
   See application file for complete search history.

(56) References Cited

U.S. PATENT DOCUMENTS 5,698,222 A * 12/1997 Mazer et al. ................. 424/464

2002/0148560 A1 * 10/2002 Carr ....................... 156/345.24

FOREIGN PATENT DOCUMENTS

JP   A 5-107186   4/1993

* cited by examiner

Primary Examiner—Tarifur Chowdhury
Assistant Examiner—Abdullahi Nur
(74) Attorney, Agent, or Firm—Roberts & Roberts, LLP

(57) ABSTRACT

An ICP analysis method for solid samples which can secure reliability of the analytical results. The present invention provides an analytical method in which a finely powdered solid sample is directly injected into an inductively coupled plasma-aided emission spectrometer, wherein standard liquid samples of known concentration of objective element are analyzed by the spectrometer to establish a calibration curve for the element; at least one standard sample of finely powdered solid of known concentration is analyzed by the spectrometer to determine a conversion factor by a given procedure; and the result of the finely powdered solid sample is corrected using the conversion factor.

12 Claims, 2 Drawing Sheets

Concentration (liquid) found from the calibration curve for liquid samples (mg/L)

DIRECT ICP EMISSION SPECTRAL ANALYSIS METHOD OF SOLID SAMPLE

FIELD OF THE INVENTION

The present invention relates to a method for direct qualitative/quantitative analyses of solid samples by ICP emission spectral analysis.

DESCRIPTION OF THE RELATED ART

Emission spectral analysis has been widely employed for qualitative/quantitative analyses of impurities present in solid metallic samples. This analytical technique excites a sample with an adequate quantity of energy to examine wavelengths of plasma emitted from the sample and detect species/quantity of an impurity element by the wavelength and intensity. Arc discharge and direct current spark discharge are generally used to produce excitation energy. These energy sources, however, may not produce a discharge temperature high enough for some elements to sufficiently evaporate and excite it to emit plasma, leading to poor analytical sensitivity. Moreover, they tend to fluctuate discharge to produce the results of insufficient reproducibility.

Therefore, application of ICP emission spectral analysis (inductively coupled plasma-aided emission spectrometry: hereinafter referred to as ICP), which has been known as a technique for analysis of liquid samples, to solid samples has been studied to replace the technique which excites a sample by arc or spark discharge. ICP dissociates argon gas by an radio frequency. induction coil to produce a plasma whose energy is used to excite a sample. It produces a high discharge temperature of 6000 K or higher, and can stably vaporize essentially all of elements and hence solve the above problems involved in the emission spectral analysis which uses arc or spark discharge.

[Patent document 1] JP-A 5-107186

DISCLOSURE OF THE INVENTION

Problems to be Solved by the Invention

ICP has been developed as a technique for analyzing liquid samples, as discussed above, and it is not always easy to directly apply it to analysis of solid samples for the following reason. In order to determine species and concentration of an ICP-analyzed element, it is necessary to fit the results (emission wavelength and intensity) to a calibration curve established beforehand. However, establishment of calibration curve for a solid sample frequently involves difficulties.

The calibration curve represents a relation between emission intensity and concentration for each element. Establishment of the calibration curve needs a plurality of standard samples of known concentration. The standard sample must be homogeneous and uniform as a whole. It is easy to prepare homogeneous liquid samples, which makes ICP suitable for analysis of liquid samples. A standard solid sample frequently suffers segregation and other defects in its structure, and hence it is not easy to prepare homogeneous solid (alloy) standard samples of different concentrations. Difficulties involved in preparation of the standard samples are reflected in reliability of the calibration curve and hence analytical results.

It is an object of the present invention to provide an ICP analysis method for solid samples which can solve the problems involved in preparation of standard samples and time-consuming analysis procedure, and secure analytical result reliability.

Means for Solving the Problems

The inventors of the present invention have found, after having extensively studied to solve the above problems, that there is a definite correlation between the result of a finely powdered solid sample and that of a liquid sample of the same concentration, and that a solid sample can be directly ICP-analyzed by correcting the analytical result based on the relation between them, achieving the present invention.

The present invention provides an analytical method in which a finely powdered solid sample is directly injected into an ICP emission spectrometer, wherein standard liquid samples of known concentration of objective element are analyzed by the spectrometer to establish the calibration curve for the element; at least one standard sample of finely powdered solid of known concentration is analyzed by the spectrometer to determine a conversion factor by a given procedure; and the result of the finely powdered solid sample is corrected using the conversion factor.

The present invention will be described in more detail. The analytical method of the present invention is characterized in that a calibration curve, established with standard liquid samples, for liquid samples containing an element which is present in a solid sample to be analyzed is established, and the calibration curve is corrected to have a standard for analysis of the solid sample. A calibration curve with liquid samples is established by the normal procedure for ICP analysis. A blank solution for establishing the calibration curve with standard liquid samples is added with an objective element to prepare the solution of different concentration. These solutions are ICP-analyzed to plot measured spectral intensity against the element concentration to establish the calibration curve. The results are preferably standardized to have a linear correlation by an adequate method, e.g., least-square method. For establishing the calibration curves with liquid samples for a plurality of elements, the sample may contain a plurality of objective elements collectively or individually.

A blank solution for a standard liquid sample is preferably water or a diluted acid. A diluted acid, when used, preferably has a concentration of 3 mols/L or less, for securing linearity of the calibration curve. For establishing a calibration curve, two or more standard liquid samples for each element may be analyzed, or samples containing a mixture of two or more elements may be analyzed. Use of a mixed sample can reduce the number of standard samples. In this case, however, it is necessary to grasp whether each element causes spectral interference or not.

For analysis of standard liquid sample, it is preferable that the sample is introduced into a plasma torch together with a carrier gas (argon) into which it is sprayed by a nebulizer, as is the case with a common liquid sample for ICP analysis.

Establishment of a calibration curve with liquid samples is followed by analysis of a standard solid sample to determine a conversion factor, for which at least one sample containing an objective element is prepared. A standard solid sample is composed of a blank solid which is incorporated (alloyed) with an objective element at a given concentration. At least one sample is necessary for at least one element. Analysis can be made with a plurality of samples containing a plurality of elements at different concentrations. A standard solid sample is preferably ICP-analyzed in the same manner as that for a solid sample using the same analyzer and conditions, which is described later.

A conversion factor is determined by one of the procedures (a) and (b) described below. It may be determined individually for a plurality of elements, or for at least one element and applied to another element.

(a) Find a concentration corresponding to an emission intensity measured for a standard solid sample based on a calibration curve with liquid samples, and use ratio of actual concentration in the standard solid sample to the found one as a conversion factor.

(b) Use a ratio of an emission intensity observed by analysis of the standard solid sample to that at the same concentration in the calibration curve established with liquid samples as a conversion factor.

A solid sample is analyzed and the result is corrected using the conversion factor established by the above procedure. It is analyzed in the same manner as that for a standard solid sample. The preferable conditions are described later.

When the conversion factor established by the procedure (a) is used for correcting the analytical result of a solid sample, the corrected concentration is plotted on the abscissa axis against a concentration on the ordinate determined by fitting a result of the solid sample in the calibration curve, to establish a linear conversion curve of concentration (liquid)-concentration (solid) with the slope as the conversion factor. Then, a concentration (liquid) is found from an analytical result (spectral intensity) of the solid sample using the calibration curve for liquid samples. A true concentration of the solid sample can be determined by fitting the result in the calibration curve with the concentration (liquid) on the abscissa axis. This correction procedure is advantageous in that it can effectively utilize the calibration curve already established for liquid samples.

When the conversion factor established by the procedure (b) is used, the calibration curve for liquid samples is corrected using the conversion factor to establish a calibration curve for solid samples, in which the analytical results are fit. This procedure plots each value in the calibration curve for liquid samples, after it is multiplied by the conversion factor, to establish a linear concentration-emission intensity correlation as a calibration curve for solid samples. Then, a spectral intensity found by analysis of the solid sample is fit in the linear correlation to determine an element concentration. This procedure newly establishes a calibration curve for solid samples based on that for liquid samples. However, it can directly correct an analytical result of solid sample.

The conversion curve and calibration curve for solid samples are established for each element. However, a conversion factor for one element can be applicable to another element, as discussed above.

The basic characteristic of the present invention lies in analysis of a solid sample which is directly injected in an ICP analyzer, after it is finely powdered, preferably by igniting using spark discharge whether it is a standard solid sample or solid sample to be analyzed, to prepare an adequate quantity of the fine particles for the ICP analysis, in which a sample is excited in a plasma to emit plasma.

The spark discharge conditions determine quantity or the like of fine particles produced. The preferable spark discharge conditions are an output of 50 to 100 mWs and frequency of 50 to 150 Hz. Values below an output of 50 mWs and frequency of 50 Hz are not enough to produce fine particles in a sufficient quantity, and also cause insufficient analytical sensitivity. It is confirmed that these levels beyond the upper limits are not needed viewed from analytical sensitivity and that an excessive output tends to cause an erroneous correction by a calibration curve.

A finely powdered solid sample is injected into a plasma torch in an ICP analyzer, preferably carried by an argon gas preferably at 0.2 to 1.0 L/minute. The inventors of the present invention have found that analytical sensitivity is affected by the carrier gas flow rate. It is preferable to set the upper limit at 1.0 L/minute or less, beyond which analytical sensitivity tends to deteriorate, more preferably at 0.5 L/minute. The lower limit of 0.2 L/minute is a minimum rate for carrying the fine particles.

Advantages Of The Invention

As discussed above, the present invention uses a calibration curve for solid samples, established by a simple correction of calibration curve with standard liquid samples. The present invention does not need a plurality of standard solid samples, which are difficult to prepare, and directly analyzes a solid sample by ICP. This invention simplifies a conventional solid sample preparation procedure for ICP analysis, in which it is dissolved in a solvent. This is particularly useful for a sample containing a sparingly soluble metal element.

ICP analysis is advantageous in that it can sufficiently excite essentially all elements to emit plasma, because of high excitation temperature which it produces. Accordingly, the present invention gives highly accurate results in analysis of solid samples. The ICP calibration curve well represents a linear correlation, and is applicable to a wide content range from trace content of 1 ppm to several tens %.

The present invention is particularly useful for precious metals. Many of them are refractory metals, and hence difficult to dissolve in a solvent for analysis. Moreover, many of them are expensive, and increase analysis cost when a plurality of standard solid samples are prepared. The present invention needs only one standard solid sample as the minimum requirement, thus reducing analytical cost.

DETAILED DESCRIPTION OF THE PREFERRED EMBODIMENT

The preferred embodiment of the present invention is described below. This embodiment prepared standard liquid samples; established a calibration curve for liquid samples by analyzing the standard liquid samples; prepared and analyzed a standard solid sample; and determined a conversion factor based on the analytical result. Next, it established a linear conversion curve (concentration (liquid)-concentration (solid)) using the conversion factor; and analyzed a solid sample of unknown concentration to determine its concentration using the conversion curve. The determined concentration was verified by fluorescent X-ray analysis. The embodiment is described in more detail below.

Preparation of Standard Liquid Samples

Each of Pt, Au, Pd, Rh, Ir and Ru was diluted 100 times with a standard atomic absorption solution (KANTO CHEMICAL CO., INC, concentration: 1000 mg/L) to prepare a standard liquid solution (concentration: 10 mg/L) for each element. Each of other elements, e.g., Al, was also diluted 100 times with an ICP standard solution containing each element (ICP multi-element standard solution IV, Merck, concentration: 1 g/L) to prepare a standard liquid solution (concentration: 10 mg/L). Analysis of standard liquid samples, and establishment of calibration curve for liquid samples The standard liquid samples prepared above were analyzed to establish a calibration curve for each element by an ICP analyzer (CIROS 120, AMETEK), in which a cyclone chamber, coaxial nebulizer and torch for high concentrations were combined, under conditions of ICP power: 1.3 kW, plasma gas flow rate: 13 L/minute, nebulizer gas flow rate: 1 L/minute and additional gas flow rate: 0.2 L/minute. The standard liquid samples (concentration: 10 mg/L each) were analyzed to establish a calibration curve for each element from spectral intensity and zero position. FIG. 1 illustrates a calibration curve for Au as one example.

Preparation of Standard Solid Sample

For preparation of a standard solid sample, Pt (purity: 99.99% or more) was incorporated with Au at an optional content (100 ppm in the embodiment), and dissolved and alloyed by an radio frequency. melting apparatus.

Analysis of Standard Solid Sample

A standard solid sample was analyzed by the ICP analyzer described above after it was finely powdered by a spark abrasion sampling apparatus (SASSy, AMETEK) illustrated in FIG. 2. The discharging conditions were spark output: 59 mWs, frequency: 75 Hz and carrier Ar gas flow rate: 0.5 L/minute. It was analyzed under the same ICP analysis conditions as those described above.

Determination of Conversion Factor, and Establishment of Conversion Curve

A conversion factor was determined using a calibration curve with standard liquid samples, established using a conversion factor determined by the procedure (a) in which the $C_S/C_L$ ratio was found, where $C_S$ is a concentration of Au in the standard solid sample and $C_L$ is a concentration found from the analytical result (intensity) of the standard solid sample using the calibration curve for liquid samples. In this embodiment, the standard solid sample (Au content: 100 ppm) had a spectral intensity of 63.8 kcps, from which its conversion factor F was 127.42 based on the calibration curve illustrated in FIG. 2. This conversion factor gave the conversion curve for Au, illustrated in FIG. 3. The conversion curves can be established for other elements individually by correcting the calibration curve for liquid samples.

Analysis 1 of Solid Sample

A plurality of Au-containing solid samples of unknown different Au content were analyzed, after the conversion curve was established, using the same analyzer and conditions as those for the standard solid sample. For correction of the analytical results, an intensity found by the direct analysis was first fit in the calibration curve with the standard liquid samples to determine the content (liquid) and then the content was fit in the conversion curve for Au with the content (liquid) on the abscissa axis to convert it into the content (solid). At the same time, the ICP analysis with the solid samples dissolved in a solvent was carried out to verify the above analytical results. The results are given in Table 1.

TABLE 1

|  | Direct analysis (the embodiments of the present invention) | Analysis of sample solutions |
| --- | --- | --- |
| Sample 1 | 5 ppm | 3 ppm |
| Sample 2 | 8 ppm | 6 ppm |
| Sample 3 | 8 ppm | 7 ppm |
| Sample 4 | 10 ppm | 11 ppm |
| Sample 5 | 11 ppm | 7 ppm |
| Sample 6 | 15 ppm | 9 ppm |
| Sample 7 | 16 ppm | 13 ppm |
| Sample 8 | 17 ppm | 10 ppm |
| Sample 9 | 17 ppm | 20 ppm |
| Sample 10 | 24 ppm | 32 ppm |
| Sample 11 | 29 ppm | 30 ppm |
| Sample 12 | 35 ppm | 34 ppm |
| Sample 13 | 99 ppm | 111 ppm |

It is confirmed, as shown in Table 1, that the direct analysis of finely powdered solid samples analyzed in this embodiment can give the results closed to those determined with sample solutions, when the conversion factor is used for the direct analysis.

Analysis 2 of Solid Sample

Sample p1 shown in Table 1 was found by Analysis 1 to contain several elements of Fe, Mn, Pb, Rh and Sn in addition to Au. Content of each element was determined using the calibration curve for the element. At the same time, the ICP analysis with sample solutions was made to compare these results with each other. The results are given in Table 2.

TABLE 2

|  | Direct analysis (the embodiments of the present invention) | Analysis of sample solutions |
| --- | --- | --- |
| Au | 5 ppm | 3 ppm |
| Fe | 4214 ppm | 4260 ppm |
| Mn | 196 ppm | 127 ppm |
| Pb | 608 ppm | 502 ppm |
| Rh | 45 ppm | 61 ppm |
| Sn | 367 ppm | 494 ppm |

The conversion curve used in this embodiment for each element was prepared based on that for Au. It is confirmed that such a conversion curve exhibits an effective correction effect, by which is meant that preparation and analysis of a number of standard solid samples are not necessary and that this embodiment represents a simple procedure. It is naturally anticipated that analytical accuracy can be improved by determining a conversion factor for each element and establishing a conversion curve based on the conversion factor. It is also considered that an averaged conversion factor of a plurality of elements may be used instead of conversion factor for each element. However, determination of a plurality of conversion factors needs a time-consuming procedure, and hence is preferably carried out in consideration of required analytical accuracy and an acceptable number of steps.

Figure 1:
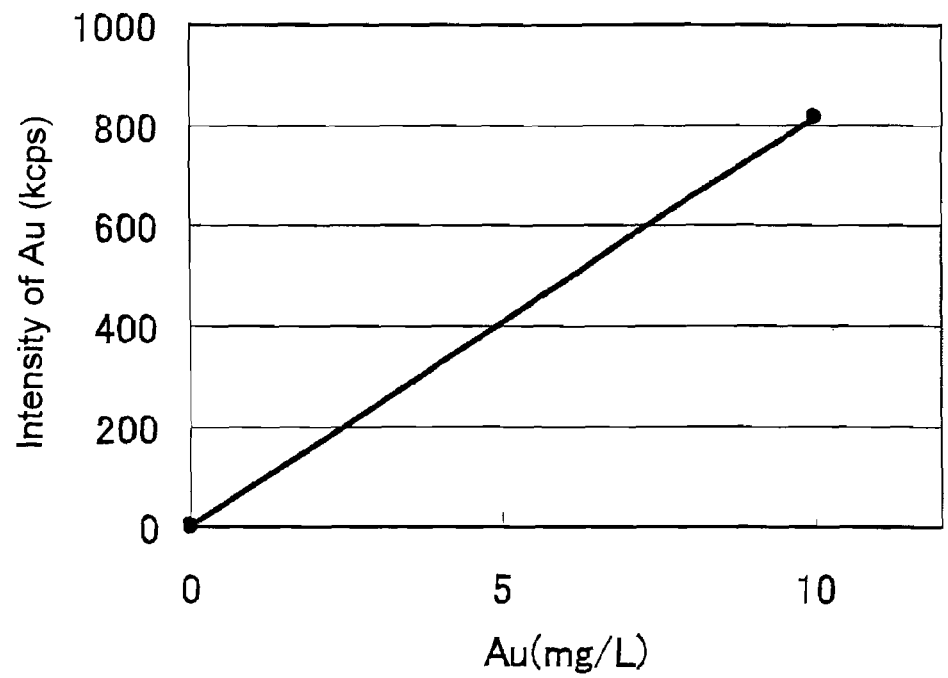
FIG. 1 illustrates a calibration curve for Au, established in this embodiment.
Figure 2:
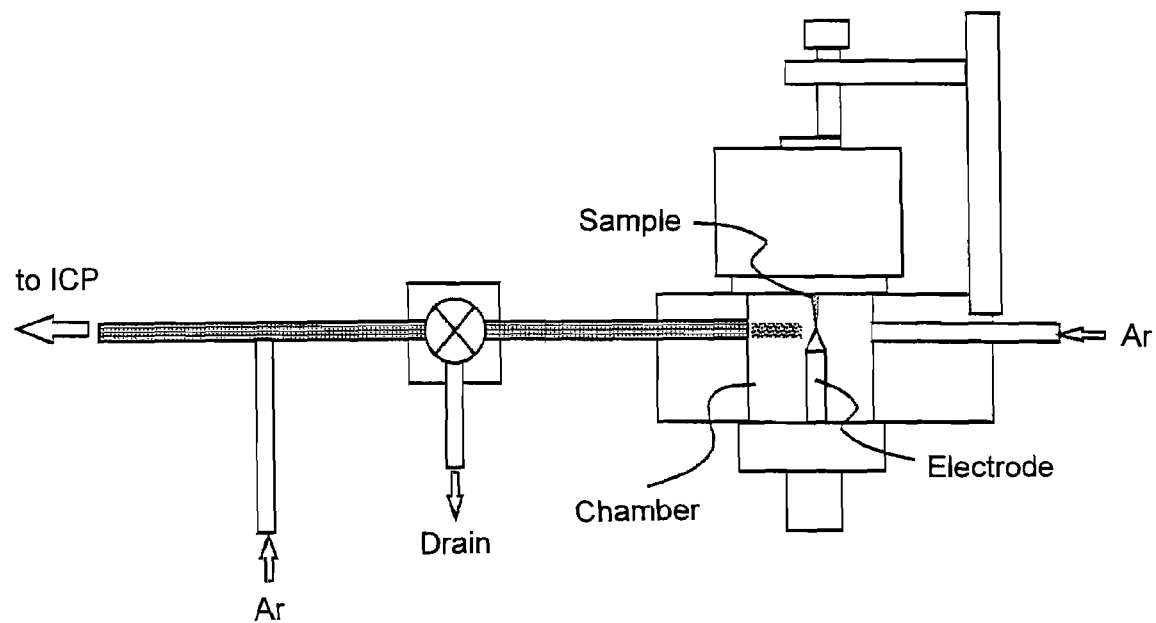
FIG. 2 illustrates an apparatus for finely powdering a solid sample used in this embodiment.
Figure 3:
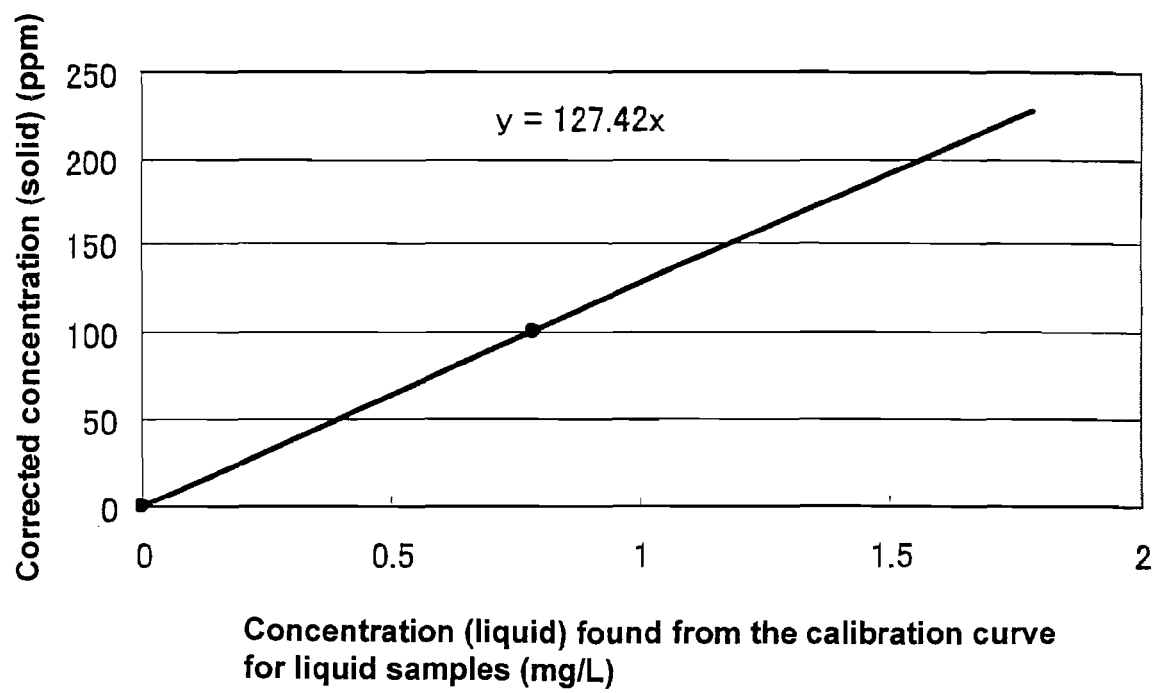
FIG. 3 illustrates a conversion curve for Au, established in this embodiment.

What is claimed is:

1. A method for analyzing a solid sample by an inductively coupled plasma-aided emission spectrometer into which the sample is directly injected after being finely powdered, comprising the steps of:

directly injecting a finely powdered solid sample together with a carrier gas into an inductively coupled plasma-aided emission spectrometer, wherein a surface of the solid sample has been subjected to a spark discharge to form a fine powder, and analyzing the finely powdered solid sample;

analyzing, by a spectrometer, standard liquid samples containing an objective element at a known concentration to establish a calibration curve for liquid samples, a chart being established for each objective element, analyzing at least one standard solid sample containing the objective element at a known concentration, after it is finely powdered, and determining a conversion factor by one of the following procedures (a) and (b), by which the result of the finely powdered solid sample is corrected using the above conversion factor:

(a) find a concentration corresponding to an emission intensity measured for a standard solid sample based on a calibration curve with liquid samples, and use ratio of actual concentration in the standard solid sample to the found one as a conversion factor, and (b) use a ratio of an emission intensity observed by analysis of the standard solid sample to that at the same concentration in the calibration curve established with liquid samples as a conversion factor.

2. The method according to claim 1, wherein the conversion factor established by the procedure (a) is used to establish a linear conversion curve of liquid concentration to solid concentration, the former being determined by fitting the result of the solid sample in the calibration curve for liquid samples and plotted on the abscissa axis, with the slope as the conversion factor, and a liquid concentration is found by fitting the analytical result of the solid sample in the calibration curve for liquid samples, and the liquid concentration is fit in the calibration curve to correct the analytical result of the solid sample.

3. The method according to claim 1, wherein the conversion factor established by the procedure (b) is used to establish a calibration curve for solid samples by multiplying each value in the calibration curve for liquid samples by the conversion factor, and a spectral intensity found by analysis of the solid sample is fit in the calibration curve for solid samples to correct the analytical result of the solid sample.

4. The method according to claim 1 wherein each of the solid sample and standard solid sample is finely powdered by spark discharge under the conditions of output: 50 to 100 mWs and frequency: 50 to 150 Hz.

5. The method according to claim 1 wherein the finely powdered solid sample is injected into the analyzer while being carried by an argon gas flowing at 0.2 to 1.0 L/minute.

6. The method according to claim 2 wherein each of the solid sample and standard solid sample is finely powdered by spark discharge under the conditions of output: 50 to 100 mWs and frequency: 50 to 150 Hz.

7. The method according to claim 3 wherein each of the solid sample and standard solid sample is finely powdered by spark discharge under the conditions of output: 50 to 100 mWs and frequency: 50 to 150 Hz.

8. The method according to claim 2 wherein the finely powdered solid sample is injected into the analyzer while being carried by an argon gas flowing at 0.2 to 1.0 L/minute.

9. The method according to claim 3 wherein the finely powdered solid sample is injected into the analyzer while being carried by an argon gas flowing at 0.2 to 1.0 L/minute.

10. The method according to claim 4 wherein the finely powdered solid sample is injected into the analyzer while being carried by an argon gas flowing at 0.2 to 1.0 L/minute.

11. The method according to claim 6 wherein the finely powdered solid sample is injected into the analyzer while being carried by an argon gas flowing at 0.2 to 1.0 L/minute.

12. The method according to claim 7 wherein the finely powdered solid sample is injected into the analyzer while being carried by an argon gas flowing at 0.2 to 1.0 L/minute.

* * * * *